US008309133B2

(12) United States Patent
Liversidge et al.

(10) Patent No.: US 8,309,133 B2
(45) Date of Patent: Nov. 13, 2012

(54) NANOPARTICULATE QUINAZOLINE DERIVATIVE FORMULATIONS

(75) Inventors: Gary G. Liversidge, West Chester, PA (US); Scott Jenkins, Downingtown, PA (US)

(73) Assignee: Alkermes Pharma Ireland Limited, Dublin (IE)

(*) Notice: Subject to any disclaimer, the term of this patent is extended or adjusted under 35 U.S.C. 154(b) by 1420 days.

(21) Appl. No.: 11/402,264

(22) Filed: Apr. 12, 2006

(65) Prior Publication Data

US 2006/0246142 A1    Nov. 2, 2006

Related U.S. Application Data

(60) Provisional application No. 60/670,429, filed on Apr. 12, 2005.

(51) Int. Cl.
*A61K 9/20* (2006.01)
*A61K 9/48* (2006.01)
(52) U.S. Cl. ......... 424/489; 424/451; 424/464; 424/465
(58) Field of Classification Search .................. None
See application file for complete search history.

(56) References Cited

U.S. PATENT DOCUMENTS

| | | | |
|---|---|---|---|
| 4,054,658 A | 10/1977 | Buehler et al. |
| 4,601,897 A | 7/1986 | Saxton |
| 4,722,938 A | 2/1988 | Sunshine et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,457,105 A | 10/1995 | Barker |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,616,582 A | 4/1997 | Barker |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,747,498 A | 5/1998 | Schnur et al. |
| 5,770,599 A | 6/1998 | Gibson |
| 5,776,496 A | 7/1998 | Violante et al. |

(Continued)

FOREIGN PATENT DOCUMENTS

EP    0 499 299    8/2000

(Continued)

OTHER PUBLICATIONS

Lindahl et al., "Characterization of Fluids from the Stomach and Proximal Jejunum in Men and Women", *Pharmaceutical Research*, vol. 14, No. 4, pp. 497-502 (1997). Fry et al., "A Specific Inhibitor of the Epidermal Growth Factor Receptor Tyrosine Kinase," *Science*, vol. 265, Aug. 1994, pp. 1093-1095.
Higgins et al., "Antitumor Activity of Erlotinib (OSI-774, Tarceva) Alone or in Combination in Human Non-Small Cell Lung Cancer Tumor Xenograft Models," 2004, pp. 503-512.
Notification of Defects for related Israel Patent Application No. 186609, dated Jan. 31, 2010.
EP Communication in related EP Patent Application No. 06740896.3, dated Feb. 8, 2011.
Notification of Defects in related Israel Patent Application No. 186609, dated Jun. 26, 2011, English Translation provided.
Wu et al., "Physical and Chemical Stability of Drug Nanoparticles," *Advanced Drug Delivery Reviews*, vol. 63, pp. 456-469 (2011).
EP Summons in related European Patent Application No. 06740897.3, dated Sep. 19, 2011.

(Continued)

*Primary Examiner* — Susan Tran
(74) *Attorney, Agent, or Firm* — Foley & Lardner LLP

(57) ABSTRACT

The present invention is directed to nanoparticulate quinazoline derivative compositions having improved pharmacokinetic profiles and reduced fed/fasted variability. The nanoparticulate quinazoline derivative particles of the composition have an effective average particle size of less than about 2000 nm and are useful in the treatment of hyperproliferative disorders, such as cancer and other neoplastic diseases. The compositions may include quinazolinamine derivatives such as erlotinib or a salt thereof.

19 Claims, No Drawings

U.S. PATENT DOCUMENTS

| | | | |
|---|---|---|---|
| 5,834,025 A | 11/1998 | De Garavilla et al. |
| 5,862,999 A | 1/1999 | Czekai et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,221,400 B1 | 4/2001 | Liversidge et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 | 11/2001 | Jain et al. |
| 6,375,986 B1 | 4/2002 | Ryde et al. |
| 6,428,814 B1 | 8/2002 | Bosch |
| 6,431,476 B1 | 8/2002 | Taylor et al. |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 | 7/2003 | Ryde et al. |
| 6,656,504 B1 | 12/2003 | Bosch et al. |
| 6,706,721 B1 | 3/2004 | Allen et al. |
| 6,742,734 B2 | 6/2004 | Reed et al. |
| 6,745,962 B2 | 6/2004 | Reed et al. |
| 6,811,767 B1 | 11/2004 | Bosch et al. |
| 6,908,626 B2 | 6/2005 | Cooper et al. |
| 6,969,529 B2 | 11/2005 | Bosch et al. |
| 6,976,647 B2 | 12/2005 | Reed et al. |
| 7,625,911 B2 * | 12/2009 | Huang | 514/266.4 |
| 2001/0016588 A1 | 8/2001 | Uckun et al. |
| 2002/0012675 A1 | 1/2002 | Jain et al. |
| 2004/0115134 A1 | 6/2004 | Merisko-Liversidge |
| 2005/0042177 A1 | 2/2005 | Ryde et al. |
| 2005/0244503 A1 | 11/2005 | Rabinow et al. |

FOREIGN PATENT DOCUMENTS

| | | |
|---|---|---|
| JP | 4-295420 | 10/1992 |
| WO | WO 93/24005 | 12/1993 |
| WO | WO 96/24340 | 8/1996 |
| WO | WO 9624340 A1 * | 8/1996 |
| WO | WO 9630347 A1 * | 10/1996 |
| WO | WO 97/14407 | 4/1997 |
| WO | WO 98/14174 | 4/1998 |
| WO | WO 9814174 A1 * | 4/1998 |
| WO | WO 03/080024 A2 | 10/2003 |
| WO | WO 03/080027 A1 | 10/2003 |
| WO | WO 03/086354 A1 | 10/2003 |
| WO | WO 03/103632 A1 | 12/2003 |
| WO | WO 03/103633 A1 | 12/2003 |
| WO | WO 03/103640 A1 | 12/2003 |
| WO | WO 2004/006959 A1 | 1/2004 |
| WO | WO 2004/041250 A2 | 5/2004 |
| WO | WO 2004/050059 A1 | 6/2004 |
| WO | WO 2004/078162 A1 | 9/2004 |
| WO | WO 2005/013937 A2 | 2/2005 |
| WO | WO 2005/016310 A1 | 2/2005 |
| WO | WO 2005014577 A1 * | 2/2005 |

OTHER PUBLICATIONS

Notice of Reasons for Rejection in related Japanese Patent Application No. 2008-506632, dated Feb. 20, 2012.
Smaill et al., "Tyrosine Kinase Inhibitors" *Journ. of Medicinal Chemistry*, vol. 43, No. 7, pp. 1380-1397 (2000).
Fujisaka et al., "International Estimation of Molecular Target Drug," Nippon Rinsho, vol. 62, No. 7, pp. 1225-1231 (2004).
Nishio, "Resistance to Target Based Therapy and Its Circumvention," Nippon Rinsho, vol. 62, No. 7, pp. 1343-1347 (2004).

* cited by examiner

NANOPARTICULATE QUINAZOLINE DERIVATIVE FORMULATIONS

CROSS-REFERENCE TO RELATED APPLICATIONS

This application claims the benefit under 35 U.S.C. §119(e) of U.S. provisional application No. 60/670,429, filed on Apr. 12, 2005, which is incorporated by reference herein in its entirety.

FIELD

The invention relates generally to anti-cancer compounds and compositions useful in the treatment of hyperproliferative conditions such as cancer and other neoplastic diseases. More specifically, the invention relates to nanoparticulate quinazoline derivative compositions, such as nanoparticulate erlotinib hydrochloride compositions. The nanoparticulate quinazoline derivative compositions have an effective average particle size of less than about 2000 nm.

BACKGROUND

A. Background Regarding Quinazoline Derivatives

The compositions disclosed herein include quinazoline derivatives and pharmaceutically acceptable salts thereof. Quinazoline derivatives and compositions thereof are described, for example, in U.S. Pat. No. 5,457,105 for "Quinazoline Derivatives Useful for Treatment of Neoplastic Disease", U.S. Pat. No. 5,616,582 for "Quinazoline Derivatives as Anti-proliferative Agents", and U.S. Pat. No. 5,770,599 for "Quinazoline Derivatives". Additionally, these patents describe processes for the preparation of quinazoline derivatives and methods of using quinazoline derivatives in the treatment of hyperproliferative diseases such as cancer.

It is known that certain quinazoline derivatives, for example, derivatives having an aniline substituent at the 4-position, derivatives having a heteroarylamino substituent at the 4-position, and derivatives having certain tricylcic compounds which comprise a 5- or 6-membered ring fused to the benzo-ring of a quinazoline, possess receptor tyrosine kinase inhibitory activity. Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Thus, inhibition of the tyrosine kinase activity of receptor tyrosine kinases by quinazoline derivatives has an anti-proliferative effect on the cell. The in vitro effect of a 4-anilinoquinazoline derivative has been disclosed by Fry et al., *Science*, 265:1093 (1994).

Erlotinib is a quinazoline derivative with the chemical name N-(3-ethynylphenyl)-6,7-bis(2-methoxyethoxy)-4-quinazolinamine. Erlotinib Hydrochloride (HCl) is offered under the registered trademark TARCEVA® by OSI Pharmaceuticals of Melville, N.Y. TARCEVA® contains erlotinib as a hydrochloride salt having the molecular formula $C_{22}H_{23}N_3O_4 \cdot HCl$ and the following structural formula:

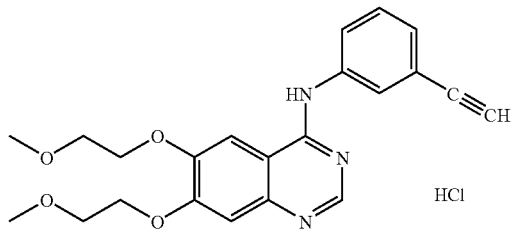

Erlotinib is described in, for example, U.S. Pat. No. 5,747,498 for "Alkynyl and Azido-Substituted 4-Anilinoquinazolines" and U.S. Pat. No. 6,706,721 for "N-(3-Ethynylphenyl)-6,7-Bis(2-Methoxyethoxy)-4-Quinazolinamine Mesylate Anhydrate and Monohydrate". U.S. Pat. No. 5,747,498 describes the compound erlotinib HCl, a pharmaceutical composition containing erlotinib HCl useful in the treatment of a hyperproliferative disorder, and a method of treating a hyperproliferative disorder which comprises administering erlotinib. U.S. Pat. No. 6,706,721 describes the anhydrate and hydrate forms of N-(3-ethynylphenyl)-6,7-bis(2-methoxyethoxy)-4-quinazolinamine mesylate compositions containing N-(3-ethynylphenyl)-6,7-bis(2-methoxyethoxy)-4-quinazolinamine mesylate, and methods of treating hyperproliferative disorders.

Like other quinazoline derivatives, erlotinib is a potent inhibitor of the erbB family of oncogenic and protooncogenic protein tyrosine kinases, such as Epidermal Growth Factor Receptor (EGFR), also known as Human Epidermal Growth Factor Receptor Type 1 (HER1). Specifically, erlotinib inhibits the tyrosine kinase activity of the EGFR signaling pathway inside the cell. It has been shown that EGFR is mutated and/or overexpressed in many human cancers such as brain, lung, squamous cell, bladder, gastric, breast, head and neck, oesophageal, gynecological, and thyroid tumors. As a result, these tumors exhibit high levels of EGFR tyrosine kinase activity. Accordingly, it has been recognized that inhibitors of EGFR are useful as selective anti-proliferative agents in mammalian cancer cells. Additionally, erlotinib inhibits the processes of angiogenesis and/or vasculogenesis of tumors.

Erlotinib has been proven effective in the treatment of patients with locally advanced or metastatic non-small cell lung cancer (NSCLC) after failure of at least one prior chemotherapy regimen.

Conventional, non-nanoparticulate erlotinib HCl tablets are administered once daily as an oral tablet and must be taken between meals, that is, at least 1 hour before or 2 hours after the ingestion of food. Absorption of erlotinib HCl increases from 60% to 100% when administered with food because the presence of food delays gastric emptying allowing more time for erlotinib HCl to dissolve and exposes the erlotinib HCl to fat in which it is more soluble.

Due to the fact that conventional, non-nanoparticulate erlotinib HCl tablets are only very slightly soluble in water at 37° C., the dissolution of conventional erlotinib HCl tablets is reduced in the fasting state as compared to the fed state. Thus, erlotinib HCl has limited bioavailability in the fasting state as compared to the fed state, which limits the therapeutic outcome for all treatments requiring erlotinib HCl. There is a need in the art for erlotinib HCl and other quinazoline derivative formulations which overcome these and other problems.

B. Background Regarding Nanoparticulate Active Agent Compositions

Nanoparticulate active agent compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent does not describe nanoparticulate compositions of quinazoline derivatives, such as erlotinib.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. Nos. 5,298,262 for "Use of Ionic Cloud Point Modifiers to Prevent Particle Aggregation During Sterilization;" 5,302,401 for "Method to Reduce Particle Size Growth During Lyophilization;" 5,318,767 for "X-Ray Contrast Compositions Useful in Medical Imaging;" 5,326,552 for "Novel Formulation For Nanoparticulate X-Ray Blood Pool Contrast Agents Using High Molecular Weight Non-ionic Surfactants;" 5,328,404 for "Method of X-Ray Imaging Using Iodinated Aromatic Propanedioates;" 5,336,507 for "Use of Charged Phospholipids to Reduce Nanoparticle Aggregation;" 5,340,564 for "Formulations Comprising Olin 10-G to Prevent Particle Aggregation and Increase Stability;" 5,346,702 for "Use of Non-Ionic Cloud Point Modifiers to Minimize Nanoparticulate Aggregation During Sterilization;" 5,349,957 for "Preparation and Magnetic Properties of Very Small Magnetic-Dextran Particles;" 5,352,459 for "Use of Purified Surface Modifiers to Prevent Particle Aggregation During Sterilization;" 5,399,363 and 5,494,683, both for "Surface Modified Anticancer Nanoparticles;" 5,401,492 for "Water Insoluble Non-Magnetic Manganese Particles as Magnetic Resonance Enhancement Agents;" 5,429,824 for "Use of Tyloxapol as a Nanoparticulate Stabilizer;" 5,447,710 for "Method for Making Nanoparticulate X-Ray Blood Pool Contrast Agents Using High Molecular Weight Non-ionic Surfactants;" 5,451,393 for "X-Ray Contrast Compositions Useful in Medical Imaging;" 5,466,440 for "Formulations of Oral Gastrointestinal Diagnostic X-Ray Contrast Agents in Combination with Pharmaceutically Acceptable Clays;" 5,470,583 for "Method of Preparing Nanoparticle Compositions Containing Charged Phospholipids to Reduce Aggregation;" 5,472,683 for "Nanoparticulate Diagnostic Mixed Carbamic Anhydrides as X-Ray Contrast Agents for Blood Pool and Lymphatic System Imaging;" 5,500,204 for "Nanoparticulate Diagnostic Dimers as X-Ray Contrast Agents for Blood Pool and Lymphatic System Imaging;" 5,518,738 for "Nanoparticulate NSAID Formulations;" 5,521,218 for "Nanoparticulate Iododipamide Derivatives for Use as X-Ray Contrast Agents;" 5,525,328 for "Nanoparticulate Diagnostic Diatrizoxy Ester X-Ray Contrast Agents for Blood Pool and Lymphatic System Imaging;" 5,543,133 for "Process of Preparing X-Ray Contrast Compositions Containing Nanoparticles;" 5,552,160 for "Surface Modified NSAID Nanoparticles;" 5,560,931 for "Formulations of Compounds as Nanoparticulate Dispersions in Digestible Oils or Fatty Acids;" 5,565,188 for "Polyalkylene Block Copolymers as Surface Modifiers for Nanoparticles;" 5,569,448 for "Sulfated Non-ionic Block Copolymer Surfactant as Stabilizer Coatings for Nanoparticle Compositions;" 5,571,536 for "Formulations of Compounds as Nanoparticulate Dispersions in Digestible Oils or Fatty Acids;" 5,573,749 for "Nanoparticulate Diagnostic Mixed Carboxylic Anydrides as X-Ray Contrast Agents for Blood Pool and Lymphatic System Imaging;" 5,573,750 for "Diagnostic Imaging X-Ray Contrast Agents;" 5,573,783 for "Redispersible Nanoparticulate Film Matrices With Protective Overcoats;" 5,580,579 for "Site-specific Adhesion Within the GI Tract Using Nanoparticles Stabilized by High Molecular Weight, Linear Poly(ethylene Oxide) Polymers;" 5,585,108 for "Formulations of Oral Gastrointestinal Therapeutic Agents in Combination with Pharmaceutically Acceptable Clays;" 5,587,143 for "Butylene Oxide-Ethylene Oxide Block Copolymers Surfactants as Stabilizer Coatings for Nanoparticulate Compositions;" 5,591,456 for "Milled Naproxen with Hydroxypropyl Cellulose as Dispersion Stabilizer;" 5,593,657 for "Novel Barium Salt Formulations Stabilized by Non-ionic and Anionic Stabilizers;" 5,622,938 for "Sugar Based Surfactant for Nanocrystals;" 5,628,981 for "Improved Formulations of Oral Gastrointestinal Diagnostic X-Ray Contrast Agents and Oral Gastrointestinal Therapeutic Agents;" 5,643,552 for "Nanoparticulate Diagnostic Mixed Carbonic Anhydrides as X-Ray Contrast Agents for Blood Pool and Lymphatic System Imaging;" 5,718,388 for "Continuous Method of Grinding Pharmaceutical Substances;" 5,718,919 for "Nanoparticles Containing the R(-) Enantiomer of Ibuprofen;" 5,747,001 for "Aerosols Containing Beclomethasone Nanoparticle Dispersions;" 5,834,025 for "Reduction of Intravenously Administered Nanoparticulate Formulation Induced Adverse Physiological Reactions;" 6,045,829 "Nanocrystalline Formulations of Human Immunodeficiency Virus (HIV) Protease Inhibitors Using Cellulosic Surface Stabilizers;" 6,068,858 for "Methods of Making Nanocrystalline Formulations of Human Immunodeficiency Virus (HIV) Protease Inhibitors Using Cellulosic Surface Stabilizers;" 6,153,225 for "Injectable Formulations of Nanoparticulate Naproxen;" 6,165,506 for "New Solid Dose Form of Nanoparticulate Naproxen;" 6,221,400 for "Methods of Treating Mammals Using Nanocrystalline Formulations of Human Immunodeficiency Virus (HIV) Protease Inhibitors;" 6,264,922 for "Nebulized Aerosols Containing Nanoparticle Dispersions;" 6,267,989 for "Methods for Preventing Crystal Growth and Particle Aggregation in Nanoparticle Compositions;" 6,270,806 for "Use of PEG-Derivatized Lipids as Surface Stabilizers for Nanoparticulate Compositions;" 6,316,029 for "Rapidly Disintegrating Solid Oral Dosage Form," 6,375,986 for "Solid Dose Nanoparticulate Compositions Comprising a Synergistic Combination of a Polymeric Surface Stabilizer and Dioctyl Sodium Sulfosuccinate;" 6,428,814 for "Bioadhesive Nanoparticulate Compositions Having Cationic Surface Stabilizers;" 6,431,478 for "Small Scale Mill;" and 6,432,381 for "Methods for Targeting Drug Delivery to the Upper and/or Lower Gastrointestinal Tract," 6,592,903 for "Nanoparticulate Dispersions Comprising a Synergistic Combination of a Polymeric Surface Stabilizer and Dioctyl Sodium Sulfosuccinate," 6,582,285 for "Apparatus for sanitary wet milling;" 6,656,504 for "Nanoparticulate Compositions Comprising Amorphous Cyclosporine;" 6,742,734 for "System and Method for Milling Materials;" 6,745,962 for "Small Scale Mill and Method Thereof;" 6,811,767 for "Liquid droplet aerosols of nanoparticulate drugs;" and 6,908,626 for "Compositions having a combination of immediate release and controlled release characteristics;" 6,969,529 for "Nanoparticulate compositions comprising copolymers of vinyl pyrrolidone and vinyl acetate as surface stabilizers;" 6,976,647 for "System and Method for Milling Materials," all of which are specifically incorporated by reference. In addition, U.S. patent application Ser. No.

20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. Nos. 4,783,484 for "Particulate Composition and Use Thereof as Antimicrobial Agent;" 4,826,689 for "Method for Making Uniformly Sized Particles from Water-Insoluble Organic Compounds;" 4,997,454 for "Method for Making Uniformly-Sized Particles From Insoluble Compounds;" 5,741,522 for "Ultrasmall, Non-aggregated Porous Particles of Uniform Size for Entrapping Gas Bubbles Within and Methods;" and 5,776,496, for "Ultrasmall Porous Particles for Enhancing Ultrasound Back Scatter."

Surface modified nanoparticles and compositions thereof useful for treating cancer and other neoplastic diseases have been described, for example, in U.S. Pat. No. 5,399,363. Such surface modified anticancer nanoparticles have been shown to exhibit reduced toxicity and/or enhanced efficacy.

The present invention relates to a nanoparticulate quinazoline derivative composition for the treatment of hyperproliferative disorders, including cancer and other neoplastic conditions.

SUMMARY

The compositions disclosed herein typically include a nanoparticulate quinazoline derivative having an effective average particle size of less than about 2000 nm and at least one surface stabilizer. The surface stabilizer is typically adsorbed on or associated with the surface of the nanoparticulate quinazoline derivative particles. Optionally, the compositions may include a pharmaceutically acceptable carrier and any suitable excipients.

The nanoparticulate quinazoline derivative compositions disclosed herein may be effective in the treatment of a number of disease or conditions, including but not limited to hyperproliferative conditions such as cancer and other neoplastic diseases. In some embodiments, the pharmaceutical composition disclosed herein may include quinazoline derivatives that are effective as kinase inhibitors, anti-inflammatory agents, as bacteriostatic agents, as inhibitors of TNF-alpha production, as inhibitors of T-cell proliferation, as anti-microbial agents, as anti-viral agents (e.g., anti-HIV agents), as anti-hypertensive agents, as anti-toxoplasmotic agents, as anti-tubercular agents, and as human adenosine receptor antagonists.

A preferred dosage form of the invention is a solid dosage form, although any pharmaceutically acceptable dosage form can be utilized.

Another aspect of the invention is directed to pharmaceutical compositions comprising a nanoparticulate quinazoline derivative. In some embodiments, the quinazoline derivative is erlotinib or a salt thereof. Erlotinib, also known as N-(3-ethynylphenyl)-6,7-bis(2-methoxyethoxy)quiazolin-4-amine hydrochloride, is sold under the trade name Tarceva®. Erlotinib is a protein kinase inhibitor. The pharmaceutical compositions disclosed herein may comprise nanoparticulate erlotinib particles, or a salt thereof, having a surface stabilizer adsorbed or associated with the surface of the drug particle.

One embodiment of the invention encompasses a nanoparticulate quinazoline derivative, such as erlotinib or a salt thereof, composition, wherein the pharmacokinetic profile of the nanoparticulate quinazoline derivative is not affected by the fed or fasted state of a subject ingesting the composition.

In yet another embodiment, the invention encompasses a nanoparticulate quinazoline derivative, such as erlotinib or a salt thereof, composition, wherein administration of the composition to a subject in a fasted state is bioequivalent to administration of the composition to a subject in a fed state.

Another embodiment of the invention is directed to a nanoparticulate quinazoline derivative (such as erlotinib or a salt thereof) pharmaceutical composition which additionally include one or more compounds useful in treating hyperproliferative disorders such as cancer and other neoplastic diseases. For example, additional compounds may include gefitinib, pertuzamib, paclitaxel, cisplatin, carboplatin, gemcitabine, bevacizumab, temozolomide, sutent, leflunomide, docetaxel, imatinib, laptinib, canertinib, doxorubincin, vatalanib, sorafenib, leucovorin, capecitabine, cetixuimab, and combinations thereof. The one or more additional compounds may be present in the pharmaceutical composition as nanoparticulate particles or in another suitable form.

This invention further discloses a method of making a nanoparticulate quinazoline derivative, such as erlotinib or a salt thereof, composition according to the invention. Such a method comprises contacting a nanoparticulate quinazoline derivative with at least one surface stabilizer for a time and under conditions sufficient to provide a nanoparticulate quinazoline derivative composition having an effective average particle size of less than about 2000 nm. The one or more surface stabilizers can be contacted with a nanoparticulate quinazoline derivative, either before, during, or after size reduction of the quinazoline derivative particle.

The present invention is also directed to methods of treatment including but not limited to hyperproliferative disorders, preferably cancer, and even more preferably non-small cell lung cancer (NSCLC), using the nanoparticulate quinazoline derivative (such as erlotinib or a salt thereof) compositions of the invention. Such methods comprise administering to a subject a therapeutically effective amount of a nanoparticulate quinazoline derivative composition according to the invention. Other methods of treatment using the nanoparticulate compositions of the invention are known to those of skill in the art.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to nanoparticulate compositions comprising a quinazoline derivative, which may include quinazolinamine derivatives, such as erlotinib or a salt thereof. The compositions comprise a quinazoline derivative and preferably at least one surface stabilizer adsorbed on or associated with the surface of the drug. The quinazoline derivative particles have an effective average particle size of less than about 2000 nm.

As taught in the '684 patent, and as exemplified in the examples below, not every combination of surface stabilizer and active agent will result in a stable nanoparticulate composition. It was surprisingly discovered that stable, nanoparticulate quinazoline derivative formulations can be made.

Advantages of the nanoparticulate quinazoline derivative, such as erlotinib or a salt thereof, formulations of the invention as compared to a conventional, non-nanoparticulate composition of the same quinazoline derivative include, but are not limited to: (1) smaller tablet or other solid dosage form size; (2) smaller doses of drug required to obtain the same pharmacological effect; (3) increased bioavailability; (4) substantially similar pharmacokinetic profiles of the quinazoline derivative compositions when administered in the fed versus the fasted state; (5) bioequivalency of the quinazoline derivative compositions when administered in the fed versus the fasted state; (6) an increased rate of dissolution for the quinazoline derivative compositions; and (7) the quinazoline derivative compositions can be used in conjunction with other active agents useful in treating hyperproliferative conditions, such as cancer and non-small cell lung cancer.

The present invention also includes nanoparticulate quinazoline derivative, such as erlotinib or a salt thereof, compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

A preferred dosage form of the invention is a solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

The present invention is described herein using several definitions, as set forth below and throughout the application.

The term "effective average particle size of less than about 2000 nm," as used herein, means that at least about 50% of the nanoparticulate quinazoline derivative particles, such as erlotinib hydrochloride, have a size of less than about 2000 nm when measured by, for example, sedimentation flow fractionation, photon correlation spectroscopy, light scattering, disk centrifugation, and other techniques known to those of skill in the art.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to stable nanoparticulate quinazoline derivative particles (such as stable erlotinib particles), "stable" connotes, but is not limited to one or more of the following parameters: (1) the particles do not appreciably flocculate or agglomerate due to interparticle attractive forces or otherwise significantly increase in particle size over time; (2) that the physical structure of the particles is not altered over time, such as by conversion from an amorphous phase to a crystalline phase; (3) that the particles are chemically stable; and/or (4) where the quinazoline derivative has not been subject to a heating step at or above the melting point of the quinazoline derivative in the preparation of the nanoparticles of the present invention.

The term "conventional" or "non-nanoparticulate active agent" shall mean an active agent which is solubilized or which has an effective average particle size of greater than about 2000 nm. Nanoparticulate active agents as defined herein have an effective average particle size of less than about 2000 nm.

The phrase "poorly water soluble drugs" as used herein refers to those drugs that have a solubility in water of less than about 30 mg/ml, less than about 20 mg/ml, less than about 10 mg/ml, or less than about 1 mg/ml.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

A. Preferred Characteristics of the Nanoparticulate Quinazoline Derivative Compositions of the Invention 1. Increased Bioavailability The nanoparticulate quinazoline derivative, such as erlotinib or a salt thereof, formulations of the invention are proposed to exhibit increased bioavailability, and require smaller doses as compared to prior conventional quinazoline derivative formulations.

In one embodiment of the invention, the nanoparticulate quinazoline derivative composition, upon administration to a mammal, produces therapeutic results at a dosage which is less than that of a non-nanoparticulate dosage form of the same quinazoline derivative.

2. Improved Pk Profiles

The invention also preferably provides compositions comprising at least one nanoparticulate quinazoline derivative, such as erlotinib or a salt thereof, having a desirable pharmacokinetic profile when administered to mammalian subjects. The desirable pharmacokinetic profile of the compositions comprising at least one quinazoline derivative, such as erlotinib or a salt thereof, preferably includes, but is not limited to: (1) a $C_{max}$ for the quinazoline derivative, such as erlotinib or a salt thereof, when assayed in the plasma of a mammalian subject following administration, that is preferably greater than the $C_{max}$ for a non-nanoparticulate formulation of the same quinazoline derivative, administered at the same dosage; and/or (2) an AUC for the quinazoline derivative, such as erlotinib or a salt thereof, when assayed in the plasma of a mammalian subject following administration, that is preferably greater than the AUC for a non-nanoparticulate formulation of the same quinazoline derivative, administered at the same dosage; and/or (3) a $T_{max}$ for the quinazoline derivative, such as erlotinib or a salt thereof, when assayed in the plasma of a mammalian subject following administration, that is preferably less than the $T_{max}$ for a non-nanoparticulate formulation of the same quinazoline derivative, administered at the same dosage. The desirable pharmacokinetic profile, as used herein, is the pharmacokinetic profile measured after the initial dose of the quinazoline derivative, such as erlotinib or a salt thereof.

3. The Pharmacokinetic Profiles of the Quinazoline Derivative Compositions of the Invention are not Affected by the Fed or Fasted State of the Subject Ingesting the Compositions The invention encompasses quinazoline derivative, such as erlotinib or a salt thereof, compositions wherein the pharmacokinetic profile of quinazoline derivative is not substantially affected by the fed or fasted state of a subject ingesting the composition. This means that there is no substantial difference in the quantity of drug absorbed or the rate of drug absorption when the nanoparticulate quinazoline derivative compositions are administered in the fed versus the fasted state.

For conventional erlotinib formulations, i.e., TARCEVA®, the absorption of erlotinib is increased by 40% when administered with food. This significant difference in absorption observed with conventional erlotinib formulations is undesirable. The erlotinib formulations of the invention overcome this problem, as the erlotinib formulations reduce or preferably substantially eliminate significantly different absorption levels when administered under fed as compared to fasting conditions.

Benefits of a dosage form which substantially eliminates the effect of food include an increase in subject convenience, thereby increasing subject compliance, as the subject does not need to ensure that they are taking a dose either with or without food. This is significant, as with poor subject compliance an increase in the medical condition for which the drug is being prescribed may be observed, i.e., non-small cell lung cancer for poor subject compliance with erlotinib.

4. Bioequivalency of Quinazoline Derivative Compositions of the Invention when Administered in the Fed Versus the Fasted State The invention also provides a nanoparticulate quinazoline derivative, such as erlotinib or a salt thereof, composition in which administration of the composition to a subject in a fasted state is bioequivalent to administration of the composition to a subject in a fed state.

The difference in absorption of the quinazoline derivative compositions of the invention, when administered in the fed versus the fasted state, preferably is less than about 40%, less than about 35%, less than about 30%, less than about 25%, less than about 20%, less than about 15%, less than about 10%, less than about 5%, or less than about 3%.

In one embodiment of the invention, the invention encompasses compositions comprising at least one nanoparticulate quinazoline derivative, wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA). Under U.S. FDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

5. Dissolution Profiles of the Quinazoline Derivative Compositions of the Invention The nanoparticulate quinazoline derivative, such as erlotinib or a salt thereof, compositions of the invention are proposed to have unexpectedly dramatic dissolution profiles. Rapid dissolution of an administered active agent is preferable, as faster dissolution generally leads to faster onset of action and greater bioavailability. To improve the dissolution profile and bioavailability of the quinazoline derivative, it would be useful to increase the drug's dissolution so that it could attain a level close to 100%.

The quinazoline derivative compositions of the invention preferably have a dissolution profile in which within about 5 minutes at least about 20% of the composition is dissolved. In other embodiments of the invention, at least about 30% or at least about 40% of quinazoline derivative composition is dissolved within about 5 minutes. In yet other embodiments of the invention, at least about 40%, at least about 50%, at least about 60%, at least about 70%, or at least about 80% of the quinazoline derivative composition is dissolved within about 10 minutes. Finally, in another embodiment of the invention, at least about 70%, at least about 80%, at least about 90%, or about 100% of the quinazoline derivative composition is dissolved within about 20 minutes.

Dissolution is preferably measured in a medium which is discriminating. Such a dissolution medium will produce two very different dissolution curves for two products having very different dissolution profiles in gastric juices; i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

6. Redispersibility Profiles of the Quinazoline Derivative Compositions of the Invention An additional feature of the quinazoline derivative, such as erlotinib or a salt thereof, compositions of the invention is that the compositions redisperse such that the effective average particle size of the redispersed quinazoline derivative particles is less than about 2 microns. This is significant, as if upon administration the quinazoline derivative compositions of the invention did not redisperse to a substantially nanoparticulate particle size, then the dosage form may lose the benefits afforded by formulating the quinazoline derivative into a nanoparticulate particle size.

This is because nanoparticulate active agent compositions benefit from the small particle size of the active agent; if the active agent does not redisperse into the small particle sizes upon administration, then "clumps" or agglomerated active agent particles are formed, owing to the extremely high surface free energy of the nanoparticulate system and the thermodynamic driving force to achieve an overall reduction in free energy. With the formation of such agglomerated particles, the bioavailability of the dosage form may fall.

Moreover, the nanoparticulate quinazoline derivative compositions of the invention exhibit dramatic redispersion of the nanoparticulate quinazoline derivative particles upon administration to a mammal, such as a human or animal, as demonstrated by reconstitution/redispersion in a biorelevant aqueous media such that the effective average particle size of the redispersed quinazoline derivative particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," Pharm. Res., 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 N, and NaCl solutions, ranging in concentration from about 0.001 to about 0.1 M, and mixtures thereof. For example, electrolyte solutions can be, but are not limited to, about 0.1 N HCl or less, about 0.01 N HCl or less, about 0.001 N HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 N HCl, 0.01 N HCl, and 0.1 N HCl correspond to pH 3, pH 2, and pH 1, respectively. Thus, a 0.01 N HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+ sodium, potassium and calcium salts of chloride.

In other embodiments of the invention, the redispersed quinazoline derivative particles of the invention (redispersed in an aqueous, biorelevant, or any other suitable media) have an effective average particle size of less than about less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. Such methods suitable for measuring effective average particle size are known to a person of ordinary skill in the art.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

7. Quinazoline Derivative Compositions Used in Conjunction with Other Active Agents The quinazoline derivative, such as erlotinib or a salt thereof, compositions of the invention can additionally comprise one or more compounds useful in treating hyperproliferative disorders, such as cancer or other neoplastic diseases, or the quinazoline derivative compositions can be administered in conjunction with such a compound. Examples of such compounds include, but are not limited to, anti-cancer agents such as mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens. For example, additional compounds may include gefitinib, pertuzamib, paclitaxel, cisplatin, carboplatin, gemcitabine, bevacizumab, temozolomide, sutent, leflunomide, docetaxel, imatinib, laptinib, canertinib, doxorubincin, vatalanib, sorafenib, leucovorin, capecitabine, cetixuimab, and combinations thereof.

B. Compositions

The invention provides compositions comprising particles of at least one quinazoline derivative, such as erlotinib or a salt thereof, and at least one surface stabilizer. The surface stabilizers preferably are adsorbed on or associated with the surface of the quinazoline derivative particles. Surface stabilizers especially useful herein preferably physically adhere on, or associate with, the surface of the nanoparticulate quinazoline derivative particles but do not chemically react with the quinazoline derivative particles or itself. Individually adsorbed molecules of the surface stabilizer are essentially free of intermolecular cross-linkages.

The present invention also includes quinazoline derivative compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

1. Quinazoline Derivatives

The compositions of the invention comprise a nanoparticulate quinazoline derivative, such as erlotinib or a salt thereof. Quiazoline has the molecular formula:

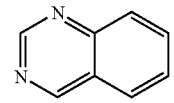

Quinazoline derivatives may include any compound that has formula I:

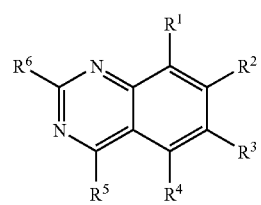

In some embodiments, quiazoline derivatives may include a compound having formula I, where each substituent $R^1$, $R^2$, $R^3$, $R^4$, $R^5$, and $R^6$, may be the same or different, and is selected, independently from each other, from a group consisting of —H; —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; -(alkylene)oxy(alkyl); —CN; —NO$_2$; —COOH; —COO(alkyl); —COO(aryl); —C(O)NH($C_{1-6}$ alkyl); —C(O)NH(aryl); sulfonyl; ($C_{1-6}$ alkyl)sulfonyl; arylsulfonyl; sulfamoyl, ($C_{1-6}$ alkyl)sulfamoyl; ($C_{1-6}$ alkyl)thio; ($C_{1-6}$ alkyl)sulfonamide; arylsulfonamide; —NHNH$_2$; —NHOH; aryl; and heteroaryl; and where each alkyl, alkenyl, alkynyl, aryl, and heteroaryl moiety may be optionally substituted with one or more groups independently selected from the group consisting of —OH; —F; —Cl; —Br; —I; —NH$_2$; alkyl- and dialkylamino; linear or branched C$_{1-6}$ alkyl, C$_{2-6}$ alkenyl and alkynyl; aralkyl; linear or branched C$_{1-6}$ alkoxy, aryloxy; aralkoxy; -(alkylene)oxy(alkyl); —CN, —NO$_2$, —COOH, —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-6}$ alkyl)thio; (C$_{1-6}$ alkyl)sulfonamide; arylsulfonamide; —NHNH$_2$; and —NHOH.

In some embodiments, the quinazoline derivative may include a quinazolinamine derivative. For example, quinazolinamine derivatives may include 4-quinazolinamine derivatives. The 4-amino group of 4-quinazolinamine derivatives optionally may be substituted with alkyl, alkenyl, alkynyl, and/or aryl groups. For example, the 4-amino group of 4-quinazolinamine derivatives may be substituted with a phenyl group, which further may be substituted with alkyl, alkenyl, alkynyl, aryl, and/or halogen groups.

In some embodiments, the 4-quinazolinamine derivatives includes one of the following substructures:

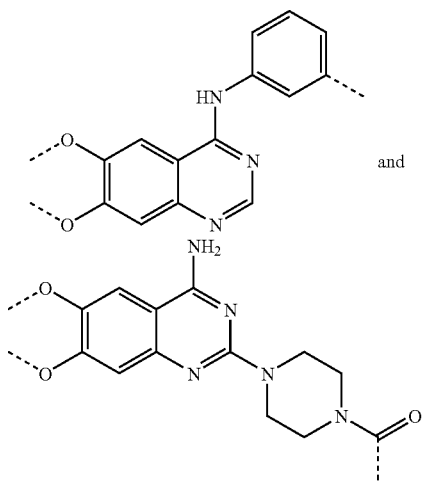

and

In some embodiments, 4-quinazolinamine derivatives having the foregoing substructures may include erlotinib, prazosin, alfuzosin, azidoprazosin, bunazosin, terazosin, tiodazosin, doxazosin, metazosin, or salts thereof.

In some embodiments, a 4-quinazolinamine derivative has formula II:

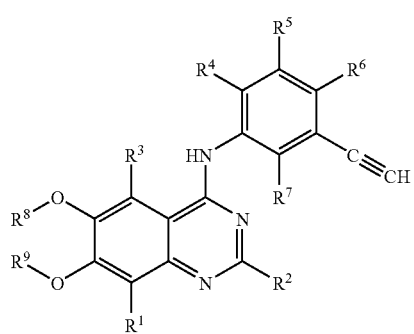

II where R$^1$, R$^2$, R$^3$, R$^4$, R$^5$, R$^6$, and R$^7$ independently are selected from the group consisting of hydrogen, C$_{1-6}$ alkyl, C$_{1-6}$ alkoxy, C$_{2-6}$ alkenyl, C$_{2-6}$ alkynyl, amino, and halogen; and R$^8$ and R$^9$ independently are selected from C$_{1-6}$ alkyl and alkylalkoxy (e.g., (C$_{1-6}$ alkyl)(C$_{1-6}$ alkoxy) such as ethylmethoxy).

In some embodiments, the quinazoline derivative or 4-quinazolinamine derivative may include compounds selected from the group consisting of 2-aryl-4-oxo-1-(4-quinazolyl)quinazolines, 3-phenyl-1-(4-quinazolyl)-1,2,3,4-tetrahydro-2,4-dioxoquinazolines, 3-phenyl-1-(4-quinazolyl)-1,2,3,4-tetrahydro-4-oxo-2-thioxoquinazolines, 2-aryl-4-oxo-1-(4-quinazolyl)-1,2,3,4-tetrahydroquinazolines, 2-aryl-1-(2-chloro-4-quinazolyl)-4-oxo-1,4-dihydroquinazolines, 4-[4-(N-substituted carbamoyl)-1-piperazinyl]-6,7-dimethoxyquinazolines, 4-chlorophenethylaminoquinazolines, [2-phenyl-4(3H)-oxo-3-quinazolinylamino]-N-substituted-arylacetamides, 4-(4'-hydroxylphenyl)-amino-6,7-dimethoxyquinazolines, 4-(3'-bromo-4'-hydroxylphenyl)-amino-6,7-dimethoxyquinazolines, 4-[[3,4-(methylenedioxy)benzyl]amino] quinazolines, 2-piperidino-4-amino-6,7-dimethoxyquinazolines, 4-amino-6,7-dimethoxy-2-(4-heterocyclylpiperazin-1-yl)quinazolines, 4-amino-6,7-dimethoxy-2-[4-(substituted oxyethoxy)piperidino]quinazolines, bis-[1,2,4]triazolo[4,3-a:4'.3'-c]quinazolines, 4-(S-butylthio)quinazolines, triazoloquinazolines, 4-(4-aryl-1-piperazinyl)quinazolines, 4-(3-substituted phenylamino)quinazolines, methoxycarbonylphenylaminoquinazoline, 2-hydrazinocarbonylphenylaminoquinazolines, 4-[4-(N-substituted (thio)carbamoyl)-1-piperazinyl]-6,7-dimethoxyquinazolines, 2-oxoimidazo[4,5-e]quinazolines, 6,7-dimethoxyquinazolines (e.g., 6-(2-methoxy)ethoxy-7-methoxyquinazolines), N-(3-ethynylphenyl)-6,7-bis(2-methoxyethoxy)-4-quinazolinamines, and mixtures thereof.

In other embodiments, the quinazoline derivative or 4-quinazolinamine derivative is selected from the group consisting of erlotinib or a salt thereof, prazosin or a salt thereof, terazosin or a salt thereof, bunazosin or a salt thereof, doxazosine or a salt thereof, trimazosine or a salt thereof, metazosin or a salt thereof, and alfuzosin or a salt thereof.

In some preferred embodiments, the quinazoline derivative is erlotinib or a salt thereof. Erlotinib, also known as N-(3-ethynylphenyl)-6,7-bis(2-methoxyethoxy)quiazolin-4-amine hydrochloride, is sold under the trade name Tarceva®. Erlotinib is a protein kinase inhibitor. The pharmaceutical compositions disclosed herein may comprise nanoparticulate erlotinib particles, or a salt thereof, having a surface stabilizer adsorbed or associated with the surface of the drug particle.

2. Surface Stabilizers

The choice of a surface stabilizer for a quinazoline derivative, such as erlotinib or a salt thereof, is non-trivial and required extensive experimentation to realize a desirable formulation. Accordingly, the present invention is directed to the surprising discovery that nanoparticulate quinazoline derivative compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, ionic, anionic, cationic, and zwitterionic compounds or surfactants.

Representative examples of surface stabilizers include hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tween® products such as e.g., Tween® 20 and Tween® 80 (ICI Speciality Chemicals)); polyethylene glycols (e.g., Carbowax® 3550 and 934 (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronic® F68 and F108, which are block copolymers of ethylene oxide and propylene oxide); poloxamines (e.g., Tetronic® 908, also known as Poloxamine™ 908, which is a tetrafunctional block copolymer derived from sequential addition of propylene oxide and ethylene oxide to ethylenediamine (BASF Wyandotte Corporation, Parsippany, N.J.)); Tetronic® 1508 (T-1508) (BASF Wyandotte Corporation), Triton® X-200, which is an alkyl aryl polyether sulfonate (Rohm and Haas); Crodestas™ F-110, which is a mixture of sucrose stearate and sucrose distearate (Croda Inc.); p-isononylphenoxypoly-(glycidol), also known as Olin®-lOG or Surfactant™ 10-G (Olin Chemicals, Stamford, Conn.); Crodestas™ SL-40 (Croda, Inc.); and SA9OHCO, which is $C_{18}H_{37}$ $CH_2(CON(CH_3)$— $CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, such as Plasdone® S630, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethyl- benzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such as benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;

(viii) two of $R_1$-$R_4$ are $CH_3$, one of $R_1$-$R_4$ is $C_6H_5CH_2$, and one of $R_1$-$R_4$ comprises at least one heteroatom;

(ix) two of $R_1$-$R_4$ are $CH_3$, one of $R_1$-$R_4$ is $C_6H_5CH_2$, and one of $R_1$-$R_4$ comprises at least one halogen;

(x) two of $R_1$-$R_4$ are $CH_3$, one of $R_1$-$R_4$ is $C_6H_5CH_2$, and one of $R_1$-$R_4$ comprises at least one cyclic fragment;

(xi) two of $R_1$-$R_4$ are $CH_3$ and one of $R_1$-$R_4$ is a phenyl ring; or (xii) two of $R_1$-$R_4$ are $CH_3$ and two of $R_1$-$R_4$ are purely aliphatic fragments.

Such compounds include, but are not limited to, benzalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The quinazoline derivative and surface stabilizer may be present in the pharmaceutical compositions disclosed herein at any suitable ratio (w/w). For example, in some embodiments the pharmaceutical compositions include the quinazoline derivative (which may include erlotinib) and the surface stabilizer at a ratio of about 20:1, 15:1, 10:1, 8:1, 7:1, 6:1, 5:1, 4:1, 3:1, 2:1 (w/w), or any range defined by said ratios (for example, but not limited to about 20:1-2:1, about 10:1-4:1, and about 8:1-5:1).

3. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Quinazoline Derivative Particle Size

The compositions of the invention comprise nanoparticulate quinazoline derivative, such as erlotinib or a salt thereof, particles which have an effective average particle size of less than about 2000 nm (i.e., 2 microns). In other embodiments of the invention, the nanoparticulate quinazoline derivative, such as erlotinib or a salt thereof, particles have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the quinazoline derivative particles have a particle size of less than the effective average, by weight, i.e., less than about 2000 nm, 1900 nm, 1800 nm, etc., when measured by the above-noted techniques. Preferably, at least about 70%, at least about 80%, at least about 90%, at least about 95%, or at least about 99% of the quinazoline derivative particles have a particle size of less than the effective average, i.e., less than about 2000 nm, 1900 nm, 1800 nm, 1700 nm, etc.

In the present invention, the value for D50 of a nanoparticulate quinazoline derivative composition is the particle size below which 50% of the quinazoline derivative particles fall, by weight. Similarly, D90 is the particle size below which 90% of the quinazoline derivative particles fall, by weight. In some embodiments of the compositions disclosed herein, the D50 is less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. In further embodiments of the compositions disclosed herein, the D90 is less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

5. Concentration of Quinazoline Derivative and Surface Stabilizers

The relative amounts of quinazoline derivative, such as erlotinib or a salt thereof, and one or more surface stabilizers can vary widely. The optimal amount of the individual components can depend, for example, upon the particular quinazoline derivative selected, the hydrophilic lipophilic balance (HLB), melting point, and the surface tension of water solutions of the stabilizer, etc.

The concentration of the quinazoline derivative can vary from about 99.5% to about 0.001%, from about 95% to about 0.1%, or from about 90% to about 0.5%, by weight, based on the total combined weight of the quinazoline derivative and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the quinazoline derivative and at least one surface stabilizer, not including other excipients.

5. Exemplary Nanoparticulate Erlotinib Tablet Formulations

Several exemplary erlotinib tablet formulations are given below. These examples are not intended to limit the claims in any respect, but rather provide exemplary tablet formulations of erlotinib which can be utilized in the methods of the invention. Such exemplary tablets can also comprise a coating agent.

Exemplary Nanoparticulate Erlotinib Tablet Formulation #1

| Component | g/Kg |
| --- | --- |
| Erlotinib | about 50 to about 500 |
| Hypromellose, USP | about 10 to about 70 |
| Docusate Sodium, USP | about 1 to about 10 |
| Sucrose, NF | about 100 to about 500 |
| Sodium Lauryl Sulfate, NF | about 1 to about 40 |
| Lactose Monohydrate, NF | about 50 to about 400 |
| Silicified Microcrystalline Cellulose | about 50 to about 300 |
| Crospovidone, NF | about 20 to about 300 |
| Magnesium Stearate, NF | about 0.5 to about 5 |

Exemplary Nanoparticulate Erlotinib Tablet Formulation #2

| Component | g/Kg |
| --- | --- |
| Erlotinib | about 100 to about 300 |
| Hypromellose, USP | about 30 to about 50 |
| Docusate Sodium, USP | about 0.5 to about 10 |
| Sucrose, NF | about 100 to about 300 |
| Sodium Lauryl Sulfate, NF | about 1 to about 30 |
| Lactose Monohydrate, NF | about 100 to about 300 |
| Silicified Microcrystalline Cellulose | about 50 to about 200 |
| Crospovidone, NF | about 50 to about 200 |
| Magnesium Stearate, NF | about 0.5 to about 5 |

Exemplary Nanoparticulate Erlotinib Tablet Formulation #3

| Component | g/Kg |
| --- | --- |
| Erlotinib | about 200 to about 225 |
| Hypromellose, USP | about 42 to about 46 |
| Docusate Sodium, USP | about 2 to about 6 |
| Sucrose, NF | about 200 to about 225 |
| Sodium Lauryl Sulfate, NF | about 12 to about 18 |
| Lactose Monohydrate, NF | about 200 to about 205 |
| Silicified Microcrystalline Cellulose | about 130 to about 135 |
| Crospovidone, NF | about 112 to about 118 |
| Magnesium Stearate, NF | about 0.5 to about 3 |

Exemplary Nanoparticulate Erlotinib Tablet Formulation #4

| Component | g/Kg |
| --- | --- |
| Erlotinib | about 119 to about 224 |
| Hypromellose, USP | about 42 to about 46 |
| Docusate Sodium, USP | about 2 to about 6 |
| Sucrose, NF | about 119 to about 224 |
| Sodium Lauryl Sulfate, NF | about 12 to about 18 |
| Lactose Monohydrate, NF | about 119 to about 224 |
| Silicified Microcrystalline Cellulose | about 129 to about 134 |
| Crospovidone, NF | about 112 to about 118 |
| Magnesium Stearate, NF | about 0.5 to about 3 |

C. Methods of Making Nanoparticulate Quinazoline Derivative Compositions

The nanoparticulate quinazoline derivative, such as erlotinib or a salt thereof, compositions can be made using, for example, milling, homogenization, precipitation, cyrogenic, or emulsion techniques. Exemplary methods of making nanoparticulate active agent compositions are described in the '684 patent. Methods of making nanoparticulate active agent compositions are also described in U.S. Pat. No. 5,518,187 for "Method of Grinding Pharmaceutical Substances;" U.S.

Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate quinazoline derivative compositions or dispersions can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

1. Milling to Obtain Nanoparticulate Quinazoline Derivative Dispersions

Milling a quinazoline derivative, such as erlotinib or a salt thereof, to obtain a nanoparticulate dispersion comprises dispersing the quinazoline derivative particles in a liquid dispersion medium in which the quinazoline derivative is poorly soluble, followed by applying mechanical means in the presence of grinding media to reduce the particle size of the quinazoline derivative to the desired effective average particle size. The dispersion medium can be, for example, water, safflower oil, ethanol, t-butanol, glycerin, polyethylene glycol (PEG), hexane, or glycol. A preferred dispersion medium is water.

The quinazoline derivative particles can be reduced in size in the presence of at least one surface stabilizer. Alternatively, the quinazoline derivative particles can be contacted with one or more surface stabilizers after attrition. Other compounds, such as a diluent, can be added to the quinazoline derivative/surface stabilizer composition during the size reduction process. Dispersions can be manufactured continuously or in a batch mode.

2. Precipitation to Obtain Nanoparticulate Quinazoline Derivative Compositions

Another method of forming the desired nanoparticulate quinazoline derivative, such as erlotinib or a salt thereof, composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the quinazoline derivative in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Quinazoline Derivative Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing particles of a quinazoline derivative, such as erlotinib or a salt thereof, in a liquid dispersion medium, followed by subjecting the dispersion to homogenization to reduce the particle size of a quinazoline derivative to the desired effective average particle size. The quinazoline derivative particles can be reduced in size in the presence of at least one surface stabilizer. Alternatively, the quinazoline derivative particles can be contacted with one or more surface stabilizers either before or after attrition. Other compounds, such as a diluent, can be added to the quinazoline derivative/surface stabilizer composition before, during, or after the size reduction process. Dispersions can be manufactured continuously or in a batch mode.

4. Cryogenic Methodologies to Obtain Nanoparticulate Quinazoline Derivative Compositions Another method of forming the desired nanoparticulate quinazoline derivative, such as erlotinib or a salt thereof, composition is by spray freezing into liquid (SFL). This technology comprises use of an organic or organoaqueous solution of quinazoline derivative with stabilizers, which is injected into a cryogenic liquid, such as liquid nitrogen. The droplets of the quinazoline derivative solution freeze at a rate sufficient to minimize crystallization and particle growth, thus forming nanostructured quinazoline derivative particles. Depending upon the choice of solvent system and processing conditions, the nanoparticulate quinazoline derivative particles can have varying particle morphology. In the isolation step, the nitrogen and solvent are removed under conditions that avoid agglomeration or ripening of the quinazoline derivative particles.

As a complementary technology to SFL, ultra rapid freezing (URF) may also be used to created equivalent nanostructured quinazoline derivative particles with greatly enhanced surface area. URF comprises an organic or organoaqueous solution of quinazoline derivative with stabilizers onto a cryogenic substrate.

5. Emulsion Methodologies to Obtain Nanoparticulate Quinazoline Derivative Compositions Another method of forming the desired nanoparticulate quinazoline derivative, such as erlotinib or a salt thereof, composition is by template emulsion. Template emulsion creates nanostructured quinazoline derivative particles with controlled particle size distribution and rapid dissolution performance. The method comprises an oil-in-water emulsion that is prepared, then swelled with a non-aqueous solution comprising the quinazoline derivative and stabilizers. The particle size distribution of quinazoline derivative particles is a direct result of the size of the emulsion droplets prior to loading with the quinazoline derivative, a property which can be controlled and optimized in this process. Furthermore, through selected use of solvents and stabilizers, emulsion stability is achieved with no or suppressed Ostwald ripening. Subsequently, the solvent and water are removed, and the stabilized nanostructured quinazoline derivative particles are recovered. Various quinazoline derivative particles morphologies can be achieved by appropriate control of processing conditions.

Published International Patent Application No. WO 97/14407 to Pace et al., published Apr. 24, 1997, discloses particles of water insoluble biologically active compounds with an average size of 100 nm to 300 nm that are prepared by dissolving the compound in a solution and then spraying the solution into compressed gas, liquid or supercritical fluid in the presence of appropriate surface modifiers.

D. Methods of Using the Quinazoline Derivative Compositions of the Invention

The invention provides a method of rapidly increasing the plasma levels of a quinazoline derivative, such as erlotinib or a salt thereof, in a subject. Such a method comprises orally administering to a subject an effective amount of a composition according to the invention comprising a nanoparticulate quinazoline derivative.

The nanoparticulate quinazoline derivative composition, in accordance with standard pharmacokinetic practice, preferably produces a maximum blood plasma concentration profile in less than about 6 hours, less than about 5 hours, less than about 4 hours, less than about 3 hours, less than about 2 hours, less than about 1 hour, or less than about 30 minutes after the initial dose of the composition.

The compositions of the invention are useful in treating hyperproliferative conditions, including but not limited to, cancers and other neoplastic diseases. Such cancers include, but are not limited to brain, lung, squamous cell, bladder, gastric, breast, head and neck, oesophageal, gynecological, and thyroid cancer. Erlotinib HCl has been indicated for the treatment of patients will locally advanced or metastatic non-small cell lung cancer (NSCLC) after failure of at least one prior chemotherapy regimen. The compositions of the invention are also useful for treatment of NSCLC.

The quinazoline derivative compositions of the invention can be administered to a subject via any conventional means including, but not limited to, orally, rectally, oticly, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate quinazoline derivative, such as erlotinib or a salt thereof, compositions may also comprise adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to a quinazoline derivative, such as erlotinib or a salt thereof, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

'Therapeutically effective amount' as used herein with respect to a quinazoline derivative dosage shall mean that dosage that provides the specific pharmacological response for which a quinazoline derivative is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that quinazoline derivative dosages are, in particular instances, measured as oral dosages, or with reference to drug levels as measured in blood.

One of ordinary skill will appreciate that effective amounts of a quinazoline derivative can be determined empirically and can be employed in pure form or, where such forms exist, in pharmaceutically acceptable salt, ester, or prodrug form. Actual dosage levels of a quinazoline derivative in the nanoparticulate compositions of the invention may be varied to obtain an amount of a quinazoline derivative that is effective to obtain a desired therapeutic response for a particular composition and method of administration. The selected dosage level therefore depends upon the desired therapeutic effect, the route of administration, the potency of the administered erlotinib, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Example 1

The purpose of this example was to prepare a nanoparticulate erlotinib composition.

An aqueous dispersion of 5% (w/w) erlotinib hydrochloride (Supplier: Camida Ltd, Tower House, New Quay, Clonmel, Co. Tipperary, Ireland; Manufacturer: Elkimia Inc. 6221, Des Rossignols, Laval, Qc, Canada, H7L 5T6), 2% (w/w) Pharmacoat® 603 (hydroxypropylmethylcellulose), and 93% (w/w) deionized water was milled in a 10 ml chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 2500 rpms for 60 min.

The milled composition was analyzed via microscopy, and the particle size of the milled erlotinib hydrochloride was measured. Microscopy was done using a Lecia DM5000B and Lecia CTR 5000 light source (Laboratory Instruments and Supplies Ltd., Ashbourne Co., Meath, Ireland). Microscopy showed that nanoparticulates of erlotinib hydrochloride were present which were susceptible to brownian motion. The majority of the sample under analysis was observed to be considerably flocculated with unmilled erlotinib hydrochloride particles present.

The particle size of the milled erlotinib hydrochloride particles was measured, in Milli Q Water, using a Horiba LA-910 Particular sciences (Hatton Derbyshire, England). Erlotinib hydrochloride particle size was measured initially and then again following 60 seconds sonication. The results are shown below in Table 1.

TABLE 1

| Sonication? | Mean (nm) | D50 (nm) | D90 (nm) | D95 (nm) |
|---|---|---|---|---|
| No | 74246 | 54704 | 167364 | 280059 |
| Yes | 100562 | 36550 | 290741 | 337455 |

This example demonstrates an unsuccessful attempt to prepare a nanoparticulate erlotinib hydrochloride composition, as the composition had a D50, before sonication, of greater than 2000 nm.

Example 2

The purpose of this example was to prepare a nanoparticulate erlotinib composition.

An aqueous dispersion of 5% (w/w) erlotinib hydrochloride, 1.25% (w/w) Plasdone® S630 (Copovidone K25-34; a random copolymer of vinyl acetate and vinyl pyrrolidone), and 0.25% (w/w) sodium lauryl sulfate was milled in a 10 mL chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 2500 rpms for 120 min.

The particle size of the milled erlotinib hydrochloride particles was measured, in Milli Q Water, using a Horiba LA-910 Particular sciences (Hatton Derbyshire, England). Erlotinib hydrochloride particle size was measured initially and then again following 60 seconds sonication. The results are shown below in Table 2.

TABLE 2

| Sonication? | Mean (nm) | D50 (nm) | D90 (nm) | D95 (nm) |
|---|---|---|---|---|
| No | 15284 | 7296 | 31617 | 59366 |
| Yes | 10803 | 5266 | 31193 | 41187 |

This example demonstrates an unsuccessful attempt to prepare a nanoparticulate erlotinib hydrochloride composition, as the composition had a D50, before sonication, of greater than 2000 nm.

Example 3

The purpose of this example was to prepare a nanoparticulate erlotinib composition.

An aqueous dispersion of 5% (w/w) erlotinib hydrochloride, 1.25% (w/w) Plasdone® K29/32 (Povidone K29/32), and 0.05% (w/w) docusate sodium was milled in a 10 mL chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 2500 rpms for 60 min.

The milled composition was analyzed via microscopy, and the particle size of the milled erlotinib hydrochloride was measured. Microscopy was done using a Lecia DM5000B and Lecia CTR 5000 light source (Laboratory Instruments and Supplies Ltd., Ashbourne Co., Meath, Ireland). Microscopy showed that the sample appeared well dispersed with nanoparticulate erlotinib hydrochloride particles visible. Brownian motion was clearly evident. There was some evidence of unmilled erlotinib hydrochloride particles. Also there may have been some evidence of crystal growth. There was no sign of flocculation.

The particle size of the milled erlotinib hydrochloride particles was measured, in Milli Q Water, using a Horiba LA-910 Particular sciences (Hatton Derbyshire, England). Erlotinib hydrochloride particle size was measured initially and then again following 60 seconds sonication. The results are shown below in Table 3.

TABLE 3

| Sonication? | Mean (nm) | D50 (nm) | D90 (nm) | D95 (nm) |
|---|---|---|---|---|
| No | 4783 | 330 | 18071 | 31192 |
| Yes | 12214 | 767 | 48223 | 66423 |

This example demonstrates a successful attempt to prepare a nanoparticulate erlotinib hydrochloride composition, as the composition had a D50, before sonication, of less than 2000 nm. However, the larger particle sizes evident in the mean, D90 and D95 measurements indicate the presence of unmilled drug particles.

Example 4

The purpose of this example was to prepare a nanoparticulate erlotinib composition.

An aqueous dispersion of 5% (w/w) erlotinib hydrochloride, 1.25% (w/w) HPC-SL (hydroxypropylcellulose), and 0.05% (w/w) docusate sodium was milled in a 10 mL chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 3500 rpms for 60 min.

The milled composition was analyzed via microscopy, and the particle size of the milled erlotinib hydrochloride was measured. Microscopy was done using a Lecia DM5000B and Lecia CTR 5000 light source (Laboratory Instruments and Supplies Ltd., Ashbourne Co., Meath, Ireland). For an undiluted sample, microscopy showed the presence of erlotinib hydrochloride nanoparticles which were discrete and susceptible to brownian motion. Some unmilled erlotinib hydrochloride particles were apparent. For a diluted sample, brownian motion was observed, and there were no signs of erlotinib hydrochloride crystal growth. Flocculation was observed and small amounts of unmilled erlotinib hydrochloride were visible.

The particle size of the milled erlotinib hydrochloride particles was measured, in Milli Q Water, using a Horiba LA-910 Particular sciences (Hatton Derbyshire, England). Erlotinib hydrochloride particle size was measured initially and then again following 60 seconds sonication. The results are shown below in Table 4.

TABLE 4

| Sonication? | Mean (nm) | D50 (nm) | D90 (nm) | D95 (nm) |
| --- | --- | --- | --- | --- |
| No | 34585 | 2342 | 107492 | 136242 |
| Yes | 33642 | 476 | 129280 | 153641 |

This example demonstrates an unsuccessful attempt to prepare a nanoparticulate erlotinib hydrochloride composition, as the composition had a D50, before sonication, of greater than 2000 nm.

Example 5

The purpose of this example was to prepare a nanoparticulate erlotinib composition.

An aqueous dispersion of 5% (w/w) erlotinib hydrochloride, 1.25% (w/w) Plasdone® S630 (Copovidone K25-34), 0.05% (w/w) sodium lauryl sulfate was milled in a 10 mL chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 2500 rpms for 120 min.

The milled composition was analyzed via microscopy. Microscopy was done using a Lecia DM5000B and Lecia CTR 5000 light source (Laboratory Instruments and Supplies Ltd., Ashbourne Co., Meath, Ireland). For an undiluted sample, microscopy showed the presence of erlotinib hydrochloride nanoparticles which were discrete and susceptible to brownian motion. Some unmilled erlotinib hydrochloride particles were apparent. For a diluted sample, brownian motion was observed, and there were no signs of erlotinib hydrochloride crystal growth. Flocculation was observed and small amounts of unmilled erlotinib hydrochloride were visible.

The particle size of the milled erlotinib hydrochloride particles was measured, in Milli Q Water, using a Horiba LA-910 Particular sciences (Hatton Derbyshire, England), for two different samples of the milled composition. Erlotinib hydrochloride particle size was measured initially and then again following 60 seconds sonication. The results are shown below in Table 5.

TABLE 5

| Sample | Sonication? | Mean (nm) | D50 (nm) | D90 (nm) | D95 (nm) |
| --- | --- | --- | --- | --- | --- |
| Sample 1 | No | 740 | 301 | 1078 | 3996 |
| Sample 1 (repeat) | No | 2236 | 324 | 6650 | 13715 |
| Sample 1 | Yes | 3665 | 414 | 13002 | 20727 |
| Sample 2 | No | 34449 | 7313 | 100410 | 116959 |
| Sample 2 | Yes | 3669 | 328 | 13333 | 25875 |

This example demonstrates a successful attempt to prepare a nanoparticulate erlotinib hydrochloride composition, as the composition had a D50, before sonication, of less than 2000 nm. However, the larger particle sizes evident in the mean, D90 and D95 measurements indicate the presence of unmilled drug particles.

Example 6

The purpose of this example was to prepare a nanoparticulate erlotinib composition.

An aqueous dispersion of 5% (w/w) erlotinib hydrochloride, 1.25% (w/w) Plasdone® K-17 (Povidone K17), and 0.05% (w/w) benzalkonium chloride was milled in a 10 mL chamber of a NanoMill® 0.01 (NanoMill Systems, King of Prussia, Pa.; see also U.S. Pat. No. 6,431,476), along with 500 micron PolyMill® attrition media (Dow Chemical) (89% media load). The mixture was milled at a speed of 2500 rpms for 120 min.

The milled erlotinib hydrochloride composition was analyzed via microscopy. Microscopy was done using a Lecia DM5000B and Lecia CTR 5000 light source (Laboratory Instruments and Supplies Ltd., Ashbourne Co., Meath, Ireland). Microscopy demonstrated the presence of erlotinib hydrochloride nanoparticles which exhibited brownian motion. There was, however, considerable flocculation observed in the nanoparticulate erlotinib hydrochloride slurry. Unmilled erlotinib hydrochloride particles were also readily apparent. The degree of flocculation was such that the sample appeared cloudy in appearance.

Particle size measurements of the milled erlotinib hydrochloride was not carried out due to the difficulty in controlling the lamp %.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A stable nanoparticulate composition comprising:
   (a) particles of erlotinib or a salt thereof having an effective average particle size of less than 1000 nm; and
   (b) at least one surface stabilizer adsorbed on the surface of the particles of erlotinib or a salt thereof,
   wherein:
   (i) the surface stabilizer is free of intermolecular crosslinkage;
   (ii) the surface stabilizer is selected from the group consisting of Povidone K29/32, docusate sodium, copovidone K25-34, sodium lauryl sulfate, and hypromellose;

(iii) erlotinib or a salt thereof is present in an amount selected from the group consisting of from about 99.5% to about 0.001%, from about 95% to about 0.1%, and from about 90% to about 0.5%, by weight, based on the total combined weight of erlotinib or a salt thereof and at least one surface stabilizer, not including other excipients;

(iv) the surface stabilizer is present in an amount selected from the group consisting of about 0.5% to about 99.999% by weight, from about 5.0% to about 99.9% by weight, and from about 10% to about 99.5% by weight, based on the total combined dry weight of erlotinib or a salt thereof and at least one surface stabilizer, not including other excipients;

(v) the composition is in a solid oral dosage form; and (vi) the composition has:
(a) a $C_{max}$ for erlotinib or a salt thereof when assayed in the plasma of a mammalian subject following administration that is greater than the $C_{max}$ for a non-nanoparticulate formulation of erlotinib or a salt thereof administered at the same dosage;
(b) the composition has an AUC for erlotinib or a salt thereof when assayed in the plasma of a mammalian subject following administration that is greater than the AUC for a non-nanoparticulate formulation of erlotinib or a salt thereof, administered at the same dosage; or
(c) the composition has a $T_{max}$ for erlotinib or a salt thereof when assayed in the plasma of a mammalian subject following administration that is less than the $T_{max}$ for a non-nanoparticulate formulation of erlotinib or a salt thereof, administered at the same dosage.

2. The composition of claim 1, wherein the nanoparticulate erlotinib particle is selected from the group consisting of a crystalline phase, an amorphous phase, a semi-crystalline phase, and mixtures thereof.

3. The composition of claim 1, wherein the effective average particle size of the nanoparticulate erlotinib particle is selected from the group consisting of less than 900 nm, less than 800 nm, less than 700 nm, less than 600 nm, less than 500 nm, less than 400 nm, less than 300 nm, less than 250 nm, less than 200 nm, less than 100 nm, less than 75 nm, and less than 50 nm.

4. The composition of claim 1, wherein the composition is formulated:
(a) into a dosage form selected from the group consisting of tablets, and capsules;
(b) into a dosage form selected from the group consisting of controlled release formulations, fast melt formulations, delayed release formulations, extended release formulations, pulsatile release formulations, and mixed immediate release and controlled release formulations; or
(c) any combination of (a), and (b).

5. The composition of claim 4, wherein the composition further comprises one or more pharmaceutically acceptable excipients, carriers, or a combination thereof.

6. The composition of claim 1, wherein the composition is bioadhesive.

7. The composition of claim 1, wherein the composition does not produce significantly different absorption levels when administered under fed as compared to fasting conditions.

8. The composition of claim 1, wherein administration of the composition to a subject in a fasted state is bioequivalent to administration of the composition to a subject in a fed state.

9. The composition of claim 1, additionally comprising one or more active agents useful for the treatment of hyperproliferative disorders.

10. The composition of claim 9, wherein the active agent is selected from a group consisting of a mitotic inhibitor, an alkylating agent, an anti-metabolite, an intercalating antibiotic, a growth factor inhibitor, a cell cycle inhibitor, an enzyme, a topoisomerase inhibitor, a biological response modifier, an anti-hormone, and an anti-androgen.

11. The composition of claim 1, wherein upon administration to a human the erlotinib or a salt thereof does not produce significantly different absorption levels when administered under fed as compared to fasting conditions.

12. The composition of claim 11, wherein administration of the composition to a subject in a fasted state is bioequivalent to administration of the composition to a subject in a fed state.

13. The composition of claim 1, wherein upon administration to a mammal the composition produces therapeutic results at a dosage which is less than that of a non-nanoparticulate dosage form of erlotinib or a salt thereof.

14. A method for the preparation of a nanoparticulate erlotinib or salt thereof composition comprising contacting particles of erlotinib or salt thereof with at least one surface stabilizer for a time and under conditions sufficient to provide a nanoparticulate erlotinib composition having an effective average particle size of less than 1000 nm and having at least one surface stabilizer adsorbed on the surface of the particles of erlotinib or a salt thereof,
wherein:
(i) the surface stabilizer is free of intermolecular crosslinkage;
(ii) the surface stabilizer is selected from the group consisting of Povidone K29/32, docusate sodium, copovidone K25-34, sodium lauryl sulfate, and hypromellose;
(iii) erlotinib or a salt thereof is present in an amount selected from the group consisting of from about 99.5% to about 0.001%, from about 95% to about 0.1%, and from about 90% to about 0.5%, by weight, based on the total combined weight of erlotinib or a salt thereof and at least one surface stabilizer, not including other excipients;
(iv) the surface stabilizer is present in an amount selected from the group consisting of about 0.5% to about 99.999% by weight, from about 5.0% to about 99.9% by weight, and from about 10% to about 99.5% by weight, based on the total combined dry weight of erlotinib or a salt thereof and at least one surface stabilizer, not including other excipients;
(v) the composition is in a solid oral dosage form; and
(vi) the composition has:
(a) a $C_{max}$ for erlotinib or a salt thereof when assayed in the plasma of a mammalian subject following administration that is greater than the $C_{max}$ for a non-nanoparticulate formulation of erlotinib or a salt thereof administered at the same dosage;
(b) the composition has an AUC for erlotinib or a salt thereof when assayed in the plasma of a mammalian subject following administration that is greater than the AUC for a non-nanoparticulate formulation of erlotinib or a salt thereof, administered at the same dosage; or
(c) the composition has a $T_{max}$ for erlotinib or a salt thereof when assayed in the plasma of a mammalian subject following administration that is less than the $T_{max}$ for a non-nanoparticulate formulation of erlotinib or a salt thereof, administered at the same dosage.

15. The method of claim 14, wherein the contacting comprises grinding, wet grinding, homogenization, freezing, template emulsion, precipitation, or a combination thereof.

16. A method for the treatment of a hyperproliferative condition comprising administering a stable nanoparticulate composition comprising:
   (a) particles of erlotinib or a salt thereof having an effective average particle size of less than 1000 nm; and
   (b) at least one surface stabilizer adsorbed on the surface of the particles of erlotinib or a salt thereof,
wherein:
   (i) the surface stabilizer is free of intermolecular crosslinkage;
   (ii) the surface stabilizer is selected from the group consisting of Povidone K29/32, docusate sodium, copovidone K25-34, sodium lauryl sulfate, and hypromellose;
   (iii) erlotinib or a salt thereof is present in an amount selected from the group consisting of from about 99.5% to about 0.001%, from about 95% to about 0.1%, and from about 90% to about 0.5%, by weight, based on the total combined weight of erlotinib or a salt thereof and at least one surface stabilizer, not including other excipients;
   (iv) the surface stabilizer is present in an amount selected from the group consisting of about 0.5% to about 99.999% by weight, from about 5.0% to about 99.9% by weight, and from about 10% to about 99.5% by weight, based on the total combined dry weight of erlotinib or a salt thereof and at least one surface stabilizer, not including other excipients;
   (v) the composition is in a solid oral dosage form; and
   (vi) the composition has:
      (a) a $C_{max}$ for erlotinib or a salt thereof when assayed in the plasma of a mammalian subject following administration that is greater than the $C_{max}$ for a non-nanoparticulate formulation of erlotinib or a salt thereof administered at the same dosage;
      (b) the composition has an AUC for erlotinib or a salt thereof when assayed in the plasma of a mammalian subject following administration that is greater than the AUC for a non-nanoparticulate formulation of erlotinib or a salt thereof, administered at the same dosage; or
      (c) the composition has a $T_{max}$ for erlotinib or a salt thereof when assayed in the plasma of a mammalian subject following administration that is less than the $T_{max}$ for a non-nanoparticulate formulation of erlotinib or a salt thereof, administered at the same dosage.

17. The method of claim 16, wherein the hyperproliferative condition is cancer.

18. The method of claim 17, wherein the cancer is non-small cell lung cancer.

19. The method of claim 16, wherein the effective average particle size of the nanoparticulate erlotinib particles is selected from the group consisting of less than 900 nm, less than 800 nm, less than 700 nm, less than 600 nm, less than 500 nm, less than 400 nm, less than 300 nm, less than 250 nm, less than 200 nm, less than 100 nm, less than 75 nm, and less than 50 nm.

* * * * *

UNITED STATES PATENT AND TRADEMARK OFFICE
CERTIFICATE OF CORRECTION

| | | |
|---|---|---|
| PATENT NO. | : 8,309,133 B2 | Page 1 of 1 |
| APPLICATION NO. | : 11/402264 | |
| DATED | : November 13, 2012 | |
| INVENTOR(S) | : Liversidge et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1463 days.

Signed and Sealed this
Fourteenth Day of October, 2014

Michelle K. Lee
*Deputy Director of the United States Patent and Trademark Office*